United States Patent
Nishino et al.

(10) Patent No.: US 8,170,178 B2
(45) Date of Patent: May 1, 2012

(54) RADIATION IMAGE CAPTURING SYSTEM, RADIATION IMAGE CAPTURING METHOD AND PROGRAM

(75) Inventors: Naoyuki Nishino, Minami-ashigara (JP); Naoki Mochizuki, Minami-ashigara (JP); Daiki Harada, Minami-ashigara (JP); Hiroshi Fukuda, Minato-ku (JP); Eiichi Kito, Minami-ashigara (JP); Yasunori Ohta, Yokohama (JP)

(73) Assignee: FUJIFILM Corporation, Tokyo (JP)

( * ) Notice: Subject to any disclaimer, the term of this patent is extended or adjusted under 35 U.S.C. 154(b) by 553 days.

(21) Appl. No.: 12/392,600

(22) Filed: Feb. 25, 2009

(65) Prior Publication Data

US 2009/0218497 A1    Sep. 3, 2009

(30) Foreign Application Priority Data

Feb. 28, 2008 (JP) .................. 2008-048366
Feb. 16, 2009 (JP) .................. 2009-033215

(51) Int. Cl.
*H05G 1/58* (2006.01)
(52) U.S. Cl. ........................................ 378/116
(58) Field of Classification Search .......... 378/116, 378/114, 115
See application file for complete search history.

(56) References Cited

U.S. PATENT DOCUMENTS

| 2003/0092980 | A1 | 5/2003 | Nitz |
| 2004/0228439 | A1 | 11/2004 | Tsujii |
| 2005/0070783 | A1 | 3/2005 | Yanagita |
| 2007/0253534 | A1* | 11/2007 | Abe .............................. 378/116 |
| 2008/0013674 | A1 | 1/2008 | Zhang et al. |

FOREIGN PATENT DOCUMENTS

| EP | 1 103 219 A2 | 5/2001 |
| JP | 2000-105297 A | 4/2000 |
| JP | 3494683 B2 | 11/2003 |
| JP | 2006-247137 A | 9/2006 |
| JP | 2007-057946 A | 3/2007 |

OTHER PUBLICATIONS

EP Communication, dated Jul. 31, 2009, issued in corresponding EP Application No. 09002751.7, 6 pages.

* cited by examiner

*Primary Examiner* — Constantine Hannaher
(74) *Attorney, Agent, or Firm* — Sughrue Mion, PLLC (57) ABSTRACT

The radiation image capturing system includes a plurality of image capturing apparatus of different specifications for capturing a radiation image of a subject, plural processors for controlling respective image capturing apparatus, a processor selector for selecting one processor from processors based on supplied capture information, an image capturing condition setting unit for setting the image capturing conditions to be appropriate for an image capturing apparatus selected from among the plurality of image capturing apparatus, and an image capturing condition changer for, when the image capturing apparatus is changed, changing the image capturing conditions to be appropriate for the changed image capturing apparatus. The processor controls the changed image capturing apparatus according to the changed image capturing conditions.

10 Claims, 9 Drawing Sheets

RADIATION IMAGE CAPTURING SYSTEM, RADIATION IMAGE CAPTURING METHOD AND PROGRAM

BACKGROUND OF THE INVENTION

1. Field of the Invention

The present invention relates to a radiation image capturing system, a radiation image capturing method, and a program for controlling a plurality of image capturing apparatus of different specifications under given image capturing conditions to capture radiation images.

2. Description of the Related Art

In the medical field, there have widely been used radiation image capturing apparatus which apply a radiation to a subject and guide the radiation that has passed through the subject to a radiation detector, which captures a radiation image from the radiation.

One known radiation detector is a stimulable phosphor panel which stores a radiation energy representative of a radiation image in a phosphor. When the stimulable phosphor panel is irradiated with stimulating light, the phosphor emits stimulated light representative of the stored radiation image. The stimulable phosphor panel with the radiation image recorded therein is supplied to a reading apparatus which reads the stored radiation image as a visible radiation image.

In sites of medical practice such as operating rooms or the like, it is necessary to read recorded radiation image information immediately from a radiation detector for the purpose of quickly and appropriately treating the patient. As a radiation detector which meets such a requirement, there has been developed a radiation detector having a solid-state detector for converting a radiation directly into an electric signal or converting a radiation into visible light with a scintillator and then converting the visible light into an electric signal to read a detected radiation image.

There are available in the art various image capturing apparatus of different specifications for capturing radiation images using radiation detectors depending on the conditions of patients as subjects to be imaged and image capturing conditions including body regions to be imaged. Those different image capturing apparatus are controlled by respective processors of specifications corresponding to the specifications of the image capturing apparatus. According to a known radiographic system, various image capturing apparatus and processors are connected to a radiology information system (RIS) by an in-house network, and patient information and image capturing conditions set by the RIS which include image capturing methods, body regions to be imaged, radiation dose, etc. are supplied to the processors, which then control the corresponding image capturing apparatus to capture radiation images (see Japanese Laid-Open Patent Publication No. 2006-247137).

There has been also proposed in the art an apparatus for applying a radiation at a constant dose to a detector, correcting the sensitivity of the detector such that the detected level from the detector reaches a predetermined level, and then capturing a radiation image based on the corrected sensitivity of the detector for thereby obtaining desired radiation image information (see Japanese Laid-Open Patent Publication No. 2007-057946).

However, the image capturing conditions set in each of the image capturing apparatus vary depending on not only the body region to be imaged, but also the specifications of the image capturing apparatus depending on its type. The operator needs to be considerably skilled in order to set image capturing conditions for obtaining desired radiation images. Particularly, it is highly difficult for doctors to grasp detailed specifications of image capturing apparatus and set image capturing conditions based on the detailed specifications. Therefore, it has been customary in the art for the doctor in charge of a patient to set an image capturing method, a body region to be imaged, etc. and thereafter for a radiological technician, who knows much about how to handle the image capturing apparatus, to select an image capturing apparatus to be used and set detailed image capturing conditions including a tube voltage, a tube current, an irradiation time, etc. which correspond to the selected image capturing apparatus and the body region to be imaged.

The above procedure for setting image capturing conditions is considerably burdensome for the radiological technician. It is highly probable for the radiological technician to make a mistake in setting image capturing conditions.

According to the related art disclosed in Japanese Laid-Open Patent Publication No. 2007-057946, only the sensitivity of the detector is corrected, but image capturing conditions are not adjusted according to a body region to be imaged and an image capturing apparatus to be used. In this case, the dose of a radiation applied to the subject remains the same irrespectively of the body region to be imaged and the sensitivity of the detector. Even if a detector of high sensitivity is used, it does not contribute to a reduction in the dose of the applied radiation, an optimization of the dose of the radiation (i.e., an appropriate exposure) or a high image quality.

SUMMARY OF THE INVENTION

It is an object of the present invention to provide a radiation image capturing system, a radiation image capturing method and a program which are capable of easily changing image capturing conditions and obtaining desired radiation image information even with a changed image capturing apparatus, specifically by automatically changing the image capturing conditions to be appropriate for the changed image capturing apparatus, in cases where image capturing conditions have been set to be appropriate for a selected image capturing apparatus, and the image capturing apparatus is thereafter changed.

According to one aspect of the present invention, a radiation image capturing system comprising a plurality of image capturing apparatus of different specifications for capturing a radiation image of a subject, a processor for controlling the image capturing apparatus according to predetermined image capturing conditions, an image capturing condition setting unit for setting the image capturing conditions to be appropriate for an image capturing apparatus selected among the plurality of image capturing apparatus, and an image capturing condition changer for, when the image capturing apparatus is changed, changing the image capturing conditions to be appropriate for the changed image capturing apparatus, wherein the processor controls the changed image capturing apparatus according to the changed image capturing conditions.

According to another aspect of the present invention, a radiation image capturing method of capturing a radiation image with a radiation image capturing system including a plurality of image capturing apparatus of different specifications for capturing a radiation image of a subject and a processor for controlling the image capturing apparatus according to predetermined image capturing conditions, the method comprising the steps of setting the image capturing conditions to be appropriate for an image capturing apparatus selected from among the plurality of image capturing apparatus, when the image capturing apparatus is changed, changing the image capturing conditions to be appropriate for the changed image capturing apparatus, and controlling the changed image capturing apparatus according to the changed image capturing conditions.

According to still another aspect of the present invention, a program for controlling a radiation image capturing system comprising a plurality of image capturing apparatus of different specifications for capturing a radiation image of a subject and a processor for controlling the image capturing apparatus according to predetermined image capturing conditions, to function as an image capturing condition setting unit for setting the image capturing conditions to be appropriate for an image capturing apparatus selected from among the plurality of image capturing apparatus, an image capturing condition changing unit for, when the image capturing apparatus is changed, changing the image capturing conditions to be appropriate for the changed image capturing apparatus, and a controlling unit for controlling the changed image capturing apparatus according to the changed image capturing conditions.

As mentioned above, according to the radiation image capturing system, the radiation image capturing method, and the program of the present invention, in cases where image capturing conditions has been set to be appropriate for a selected image capturing apparatus, and the image capturing apparatus is thereafter changed, the set image capturing conditions can be automatically changed to image capturing conditions appropriate for the changed image capturing apparatus. Thus, image capturing conditions can easily be changed, and also, desired radiation image information can be obtained even with the changed image capturing apparatus.

When the image capturing apparatus to be used is switched to an image capturing apparatus which incorporates a radiation detector of high sensitivity, the radiation image capturing system is capable of automatically reducing the dose of a radiation to be applied to the subject without requiring the radiological technician in charge of the radiation image capturing system to perform a tedious and time-consuming procedure for changing the dose of the radiation.

With the present invention, operating efficiency for a radiation image capturing process is improved, inconvenience such as keeping the patient waiting for a long time is prevented, and a work burden of the radiological technician is reduced.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
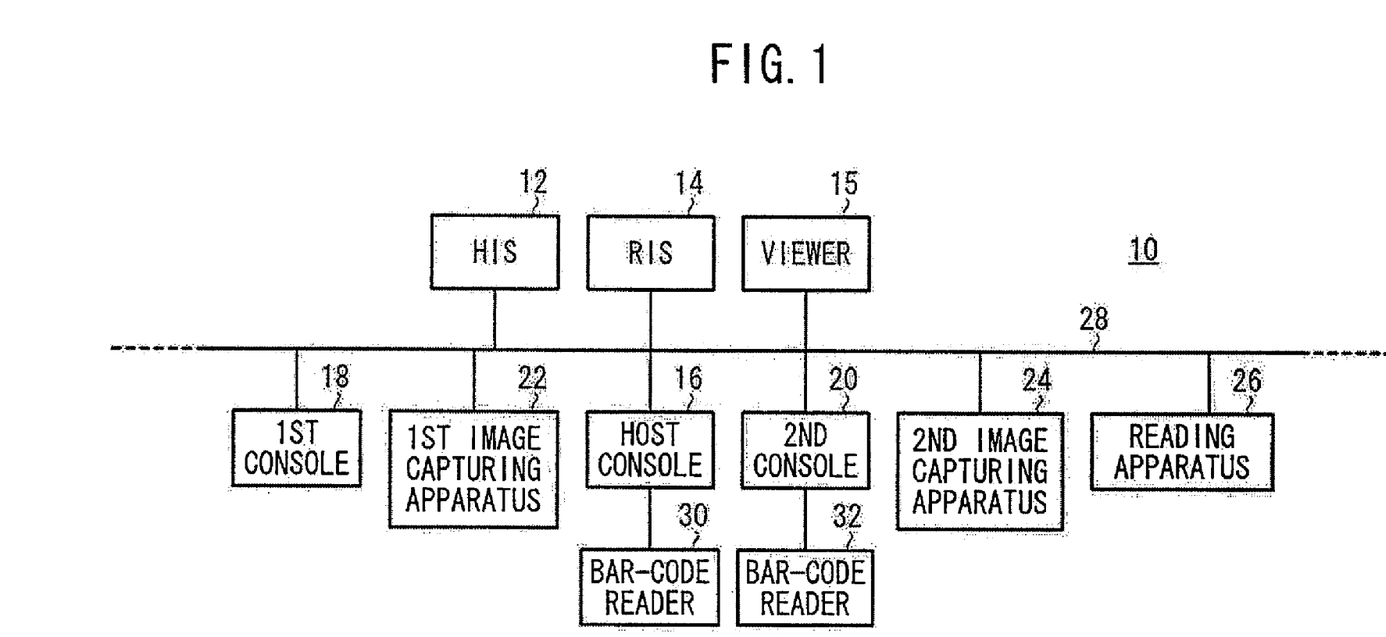
FIG. 1 is a block diagram of a radiation image capturing system according to an embodiment of the present invention.
Figure 2:
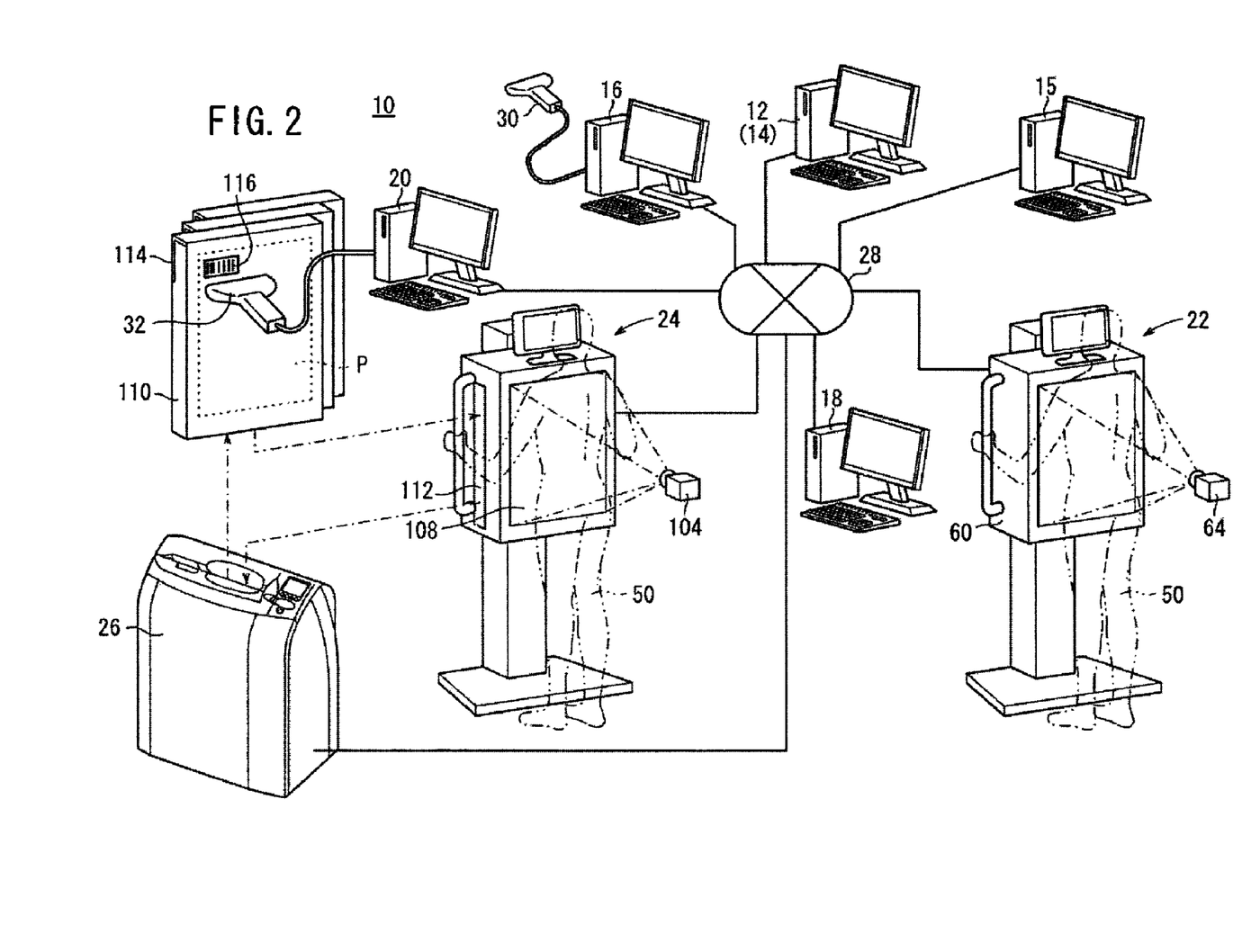
FIG. 2 is a schematic perspective view of the radiation image capturing system.

FIGS. 1 and 2 show a configuration of a radiation image capturing system 10 according to an embodiment of the present invention. As shown in FIGS. 1 and 2, the radiation image capturing system 10 comprises a hospital information system (HIS) 12 for managing medical information processing (including medical coding) in a hospital, a radiology information system (RIS) 14 for managing radiation image capturing processes performed in the radiological department of the hospital under the management of the HIS 12, a viewer 15 for displaying radiation images to be interpreted by the doctor for diagnosis, a host console (managing apparatus) 16 placed in a control room near image capturing rooms in the radiological department, for managing various image capturing apparatus of different specifications, a first console (processor) 18 and a second console (processor) 20 placed in the control room for controlling particular image capturing apparatus, respectively, a first image capturing apparatus 22 for being controlled by the first console 18, a second image capturing apparatus 24 for being controlled by the second console 20, and a reading apparatus 26 for being controlled by the second console 20 to read radiation image information captured by the second image capturing apparatus 24. The above components of the radiation image capturing system 10 are interconnected by an in-house network 28 in the hospital. If necessary, other consoles, other image capturing apparatus, and components may also be connected to the in-house network 28.

The host console 16 acquires patient information such as the name, gender, age, etc. of a patient which has been set using the HIS 12, and image capturing instruction information such as a method of capturing a radiation image, a body region to be imaged, an image capturing apparatus to be used to capture a radiation image, etc., which has been set by the doctor or radiological technician using the RIS 14, and, if necessary, image capturing conditions such as a tube voltage, a tube current, an irradiation time, etc. to be set in the radiation source of the image capturing apparatus to be used, through the in-house network 28, and supplies the acquired information to the first console 18 or the second console 20. The host console 16 may be programmed to perform the processing sequence of the first console 18 or the second console 20. If the host console 16 is programmed to perform the processing sequence of the first console 18 or the second console 20, then since the first console 18 or the second console 20 may be dispensed with, the radiation image capturing system will become less costly. To the host console 16 and the second console 20, there are connected respective bar-code readers 30, 32 for acquiring ID information for identifying a radiation detector, described later, to be used in the second image capturing apparatus 24.

Figure 3:
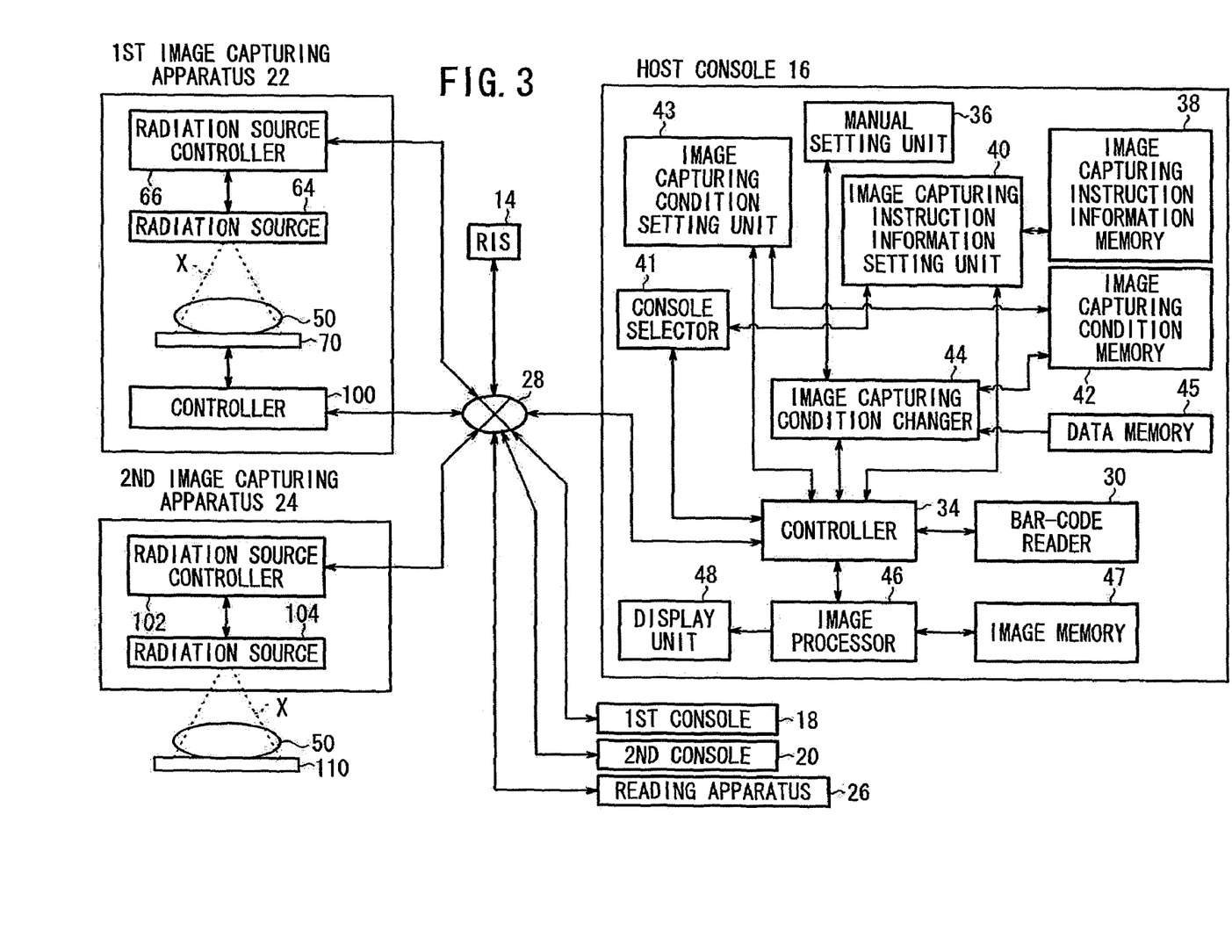
FIG. 3 is a block diagram of an assembly of a host console, a first image capturing apparatus and a second image capturing apparatus in the radiation image capturing system.

FIG. 3 shows in block form an assembly of the host console 16, the first image capturing apparatus 22, and the second image capturing apparatus 24.

The host console (image capturing condition setting apparatus) 16 has a controller 34 which sends information to and receives information from the RIS 14, the first console 18 (processor), the second console 20 (processor), the first image capturing apparatus 22, the second image capturing apparatus 24, and the reading apparatus 26. The host console 16 comprises a manual setting unit 36, an image capturing instruction information setting unit 40 for setting image capturing instruction information through the manual setting unit 36 or receiving image capturing instruction information set by the RIS 14 and storing the image capturing instruction information in an image capturing instruction information memory 38, a console selector (image capturing apparatus selector, processor selector) 41 for selecting a certain console for processing radiation image information according to the set image capturing instruction information and supplying the corresponding image capturing instruction information to the selected console, an image capturing condition setting unit 43 for setting image capturing conditions for an image capturing apparatus controlled by the selected console (i.e., an image capturing apparatus to be used) and storing the image capturing conditions in an image capturing condition memory 42, an image capturing condition changer 44 for, when the image capturing apparatus has been changed, automatically changing the image capturing conditions to be appropriate for the changed image capturing apparatus based on at least information about the changed image capturing apparatus, a data memory 45 used in the image capturing condition changer 44 for storing image capturing conditions depending on the image capturing apparatus, an image processor 46 for processing radiation image information acquired from each of the image capturing apparatus, an image memory 47 for storing the processed radiation image information from the image processor 46 or another console, and a display unit 48 for displaying the radiation image information.

The first console 18 and the second console 20 have essentially the same functions as the host console 16 except for a function for acquiring image capturing instruction information from the RIS 14, a function for selecting a console and a function for changing image capturing conditions. The configurations of the host console 16, the first console 18, and the second console 20 may not necessarily be different from each other, but may be identical to each other.

The first image capturing apparatus 22 is an upstanding image capturing apparatus for capturing a radiation image of the chest or the like of a subject 50. The first image capturing apparatus 22 comprises a radiation source 64 for being controlled by a radiation source controller 66 and an image capturing base 60 disposed in confronting relation to the radiation source 64. The image capturing base 60 houses therein a radiation detector which comprises a solid-state detecting device to be described later. The radiation source controller 66 controls the radiation source 64 according to image capturing conditions set by the host console 16.

Figure 4:
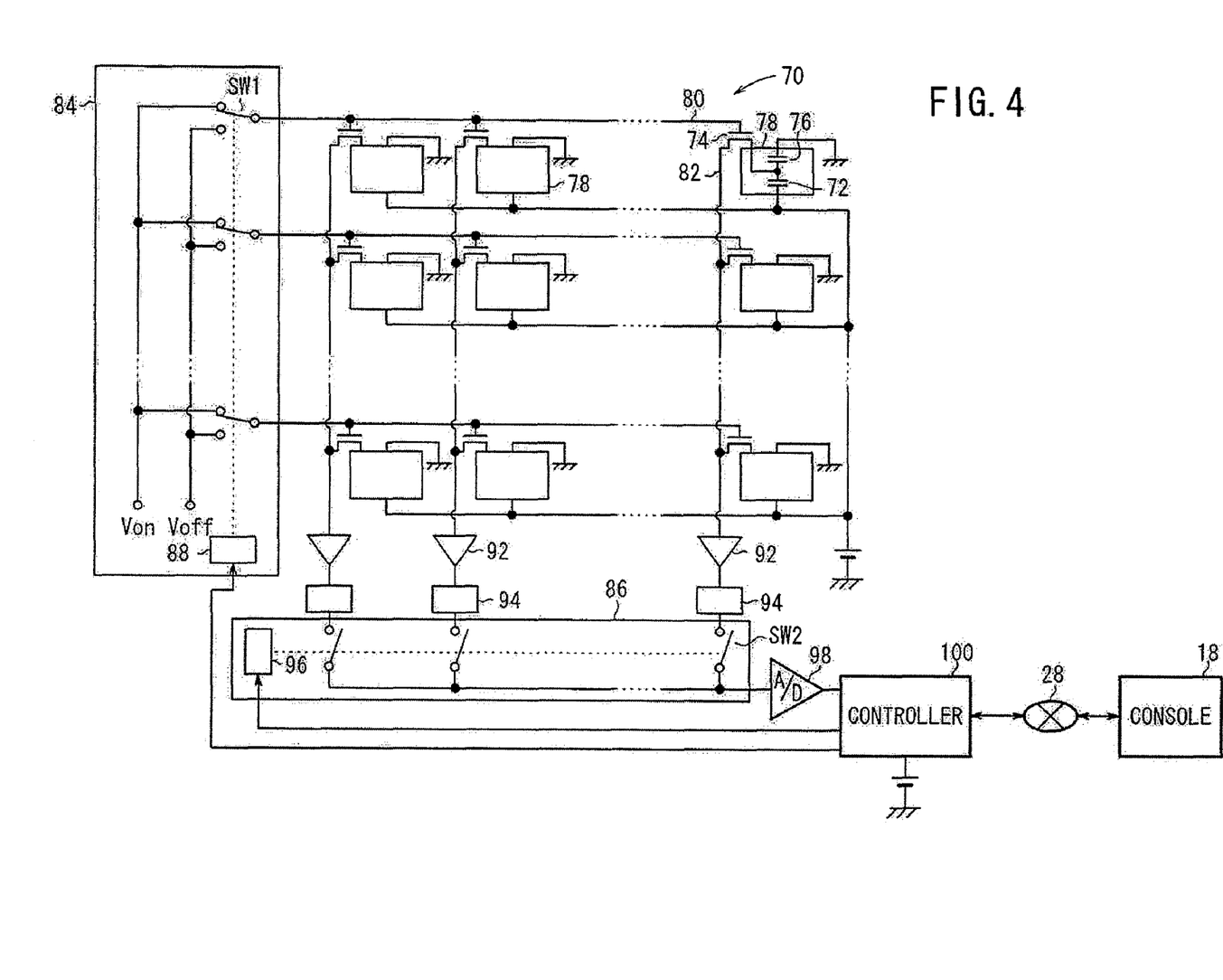
FIG. 4 is a block diagram of a circuit arrangement representative of a radiation detector.

FIG. 4 shows in block form a circuit arrangement of a radiation detector 70 housed in the image capturing base 60.

The radiation detector 70 comprises an array of thin-film transistors (TFTs) 74 arranged in rows and columns, a photoelectric conversion layer 72 made of a material such as amorphous selenium (a-Se) for generating electric charges upon detection of a radiation, the photoelectric conversion layer 72 being disposed over the array of TFTs 74, and an array of storage capacitors 76 connected to the photoelectric conversion layer 72. When the radiation is applied to the radiation detector 70, the photoelectric conversion layer 72 generates electric charges, and the storage capacitors 76 store the generated electric charges. Then, the TFTs 74 are turned on along each row at a time to read the electric charges from the storage capacitors 76 as an image signal. In FIG. 4, the photoelectric conversion layer 72 and one of the storage capacitors 76 are shown as a pixel 78, and the pixel 78 is connected to one of the TFTs 74. Details of the other pixels 78 are omitted from illustration. Since amorphous selenium tends to change its structure and lose its function at high temperatures, it needs to be used within a certain temperature range. Therefore, some means for cooling the radiation detector 70 should preferably be provided in the image capturing base 60.

The TFTs 74 connected to the respective pixels 78 are connected to respective gate lines 80 extending parallel to the rows and respective signal lines 82 extending parallel to the columns. The gate lines 80 are connected to a line scanning driver 84, and the signal lines 82 are connected to a multiplexer 86 serving as a reading circuit.

The gate lines 80 are supplied with control signals Von, Voff for turning on and off the TFTs 74 along the rows from the line scanning driver 84. The line scanning driver 84 comprises a plurality of switches SW1 for switching between the gate lines 80 and an address decoder 88 for outputting a selection signal for selecting one of the switches SW1 at a time. The address decoder 88 is supplied with an address signal from a controller 100.

The signal lines 82 are supplied with electric charges stored in the storage capacitors 76 of the pixels 78 through the TFTs 74 arranged in the columns. The electric charges supplied to the signal lines 82 are amplified by amplifiers 92 connected respectively to the signal lines 82. The amplifiers 92 are connected through respective sample and hold circuits 94 to the multiplexer 86. The multiplexer 86 comprises a plurality of switches SW2 for successively switching between the signal lines 82 and an address decoder 96 for outputting a selection signal for selecting one of the switches SW2 at a time. The address decoder 96 is supplied with an address signal from the controller 100. The multiplexer 86 has an output terminal connected to an A/D converter 98. A radiation image signal generated by the multiplexer 86 based on the electric charges from the sample and hold circuits 94 is converted by the A/D converter 98 into a digital image signal representing radiation image information, which is supplied to the controller 100. The controller 100 supplies the acquired radiation image information through the in-house network 28 to the first console 18 which controls the first image capturing apparatus 22.

The second image capturing apparatus 24 is an upstanding image capturing apparatus for capturing a radiation image of the chest or the like of a subject 50. The second image capturing apparatus 24 comprises a radiation source 104 for being controlled by a radiation source controller 102 and an image capturing base 108 disposed in confronting relation to the radiation source 104. The image capturing base 108 has a slot 112, defined in a side wall thereof, through which a cassette 110 housing a stimulable phosphor panel P therein can be loaded into the image capturing base 108. The second image capturing apparatus 24 is controlled by the second console 20 through the in-house network 28. The second image capturing apparatus 24 has different specifications from the first image capturing apparatus 22. The radiation source controller 102 controls the radiation source 104 according to image capturing conditions set by the host console 16.

The stimulable phosphor panel P comprises a support body and a stimulable phosphor layer disposed on the support body. The stimulable phosphor layer stores the energy of a radiation X that is applied thereto. When the stimulable phosphor layer is irradiated with stimulating light, it emits stimulated light depending on the stored energy. When the stimulable phosphor layer is irradiated with erasing light, it discharges any remaining energy stored therein and can be reused.

The stimulable phosphor panel P housed in the cassette 110 is removable from the cassette 110 when a lid member 114 on the cassette 110 is opened. A bar code 116 which records therein identification information including an identification number for identifying the stimulable phosphor panel P housed in the cassette 110, the size of the stimulable phosphor panel P, the sensitivity of the stimulable phosphor panel P, etc. is applied to an outer surface of the cassette 110. The bar code 116 can be read by the bar-code reader 32 connected to the second console 20 or the bar-code reader 30 connected to the host console 16.

Figure 5:
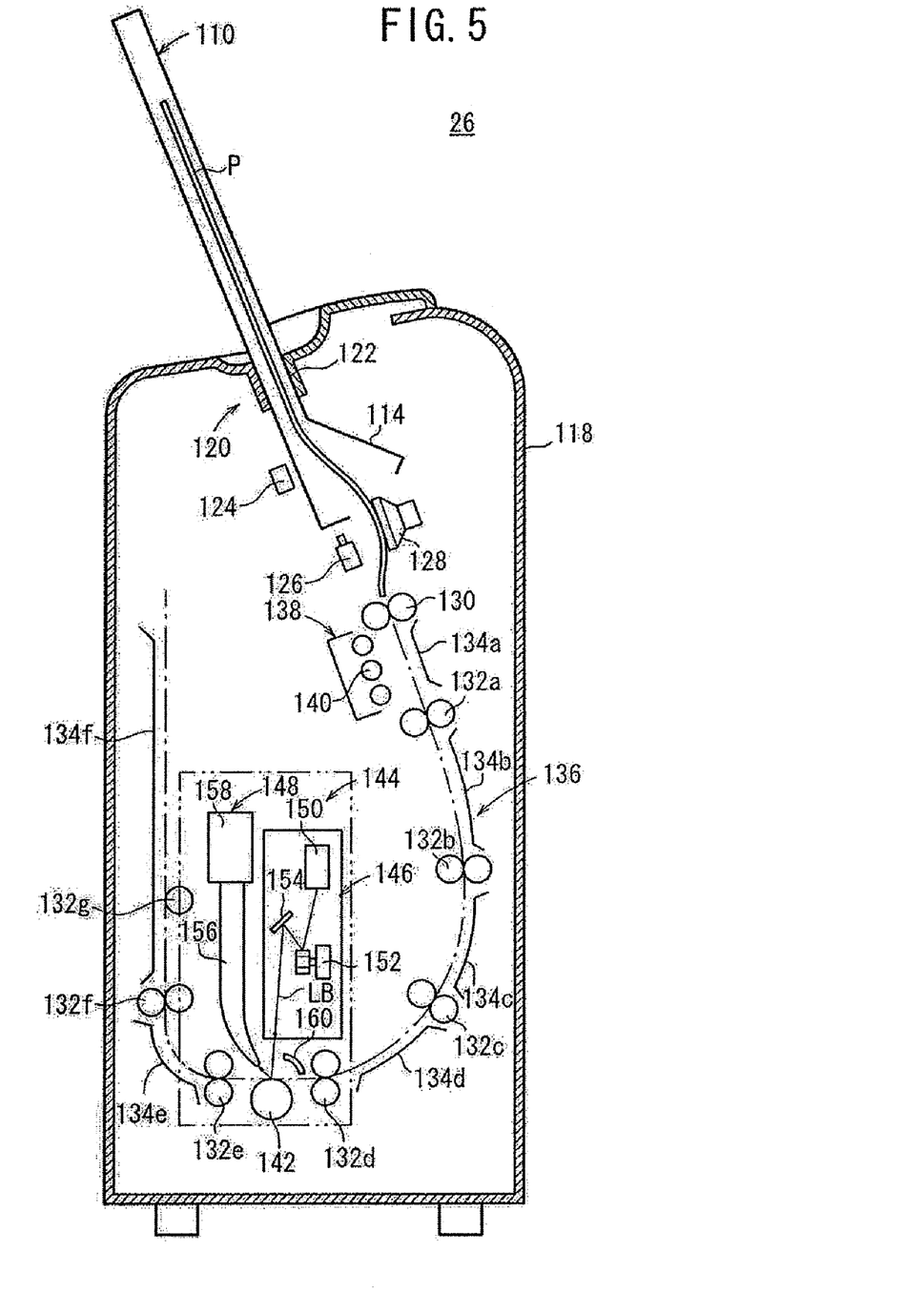
FIG. 5 is a vertical cross-sectional view of a reading apparatus of the radiation image capturing system.

Radiation image information that has been recorded in the stimulable phosphor panel P is read by the reading apparatus 26 which is constructed as shown in FIG. 5. The reading apparatus 26 as well as the second image capturing apparatus 24 is controlled by the second console 20 through the in-house network 28.

As shown in FIG. 5, the reading apparatus 26 has a cassette loader 120 disposed in an upper portion of a casing 118 and having a loading slot 122 for receiving therein the cassette 110 which houses therein the stimulable phosphor panel P with recorded radiation image information. The casing 118 of the reading apparatus 26 accommodates therein, near the loading slot 122, a bar-code reader 124 for reading the identification information recorded in the bar code 116 on the cassette 110, an unlock mechanism 126 for unlocking the lid member 114 of the cassette 110, a suction cup 128 for attracting and removing the stimulable phosphor panel P from the cassette 110 at the time the lid member 114 is opened, and a pair of nip rollers 130 for gripping and feeding the stimulable phosphor panel P removed by the suction cup 128.

The nip rollers 130 are followed by a plurality of feed rollers 132a through 132g and a plurality of guide plates 134a through 134f which jointly make up a curved feed path 136. The curved feed path 136 extends downwardly from the cassette loader 120, then extends substantially horizontally at its lowermost portion, and then extends substantially vertically upwardly. The curved feed path 136 thus shaped is effective to make the reading apparatus 26 small in size.

Between the nip rollers 130 and the feed rollers 132a, there is disposed an erasing unit 138 for erasing radiation image information remaining in the stimulable phosphor panel P from which desired radiation image information has been read. The erasing unit 138 has a plurality of erasing light sources 140 such as cold cathode tubes or the like for emitting erasing light.

A platen roller 142 is disposed between the feed rollers 132d, 132e which are positioned in the lowermost portion of the curved feed path 136. The platen roller 142 is disposed beneath a scanning unit 144 for reading the desired radiation image information recorded in the stimulable phosphor panel P.

The scanning unit 144 comprises a stimulator 146 for emitting a laser beam LB as stimulating light to scan the stimulable phosphor panel P and a reader 148 for reading stimulated light emitted from the stimulable phosphor panel P which is stimulated by the laser beam LB, the stimulated light being representative of the radiation image information.

The stimulator 146 comprises a laser oscillator 150 for outputting the laser beam LB, a rotary polygon mirror 152 for deflecting the laser beam LB in a main scanning direction across the stimulable phosphor panel P, and a reflecting mirror 154 for reflecting the laser beam LB to the stimulable phosphor panel P as it passes over the platen roller 142.

The reader 148 comprises a light guide 156 having a lower end disposed near the stimulable phosphor panel P over the platen roller 142, and a photomultiplier 158 connected to an upper end of the light guide 156 for converting the stimulated light from the stimulable phosphor panel P into an electric signal which represents the radiation image information stored in the stimulable phosphor panel P. A light collecting mirror 160 for collecting the stimulated light from the stimulable phosphor panel P is disposed near the lower end of the light guide 156. The photomultiplier 158 supplies the electric signal representing the radiation image information to the second console 20 through the in-house network 28.

A recumbent image capturing apparatus which employs the radiation detector 70 or the stimulable phosphor panel P may be connected to the in-house network 28. Furthermore, image capturing apparatus of other specifications, such as a CT apparatus, an MR apparatus, etc. may also be connected to the in-house network 28, and consoles (processors) for controlling these image capturing apparatus may also be connected to the in-house network 28.

The radiation image capturing system 10 according to the present invention is basically constructed as described above. Operation of the radiation image capturing system 10 will be described below with reference to FIGS. 6 to 9.

First, patient information such as the name, gender, age, etc. of a patient is set using the HIS 12 (step S1 in FIG. 6), and image capturing instruction information such as a method of capturing a radiation image, a body region to be imaged, and an image capturing apparatus to be used to capture a radiation image, is set in relation to the patient information using the RIS 14 (step S2).

Figure 6:
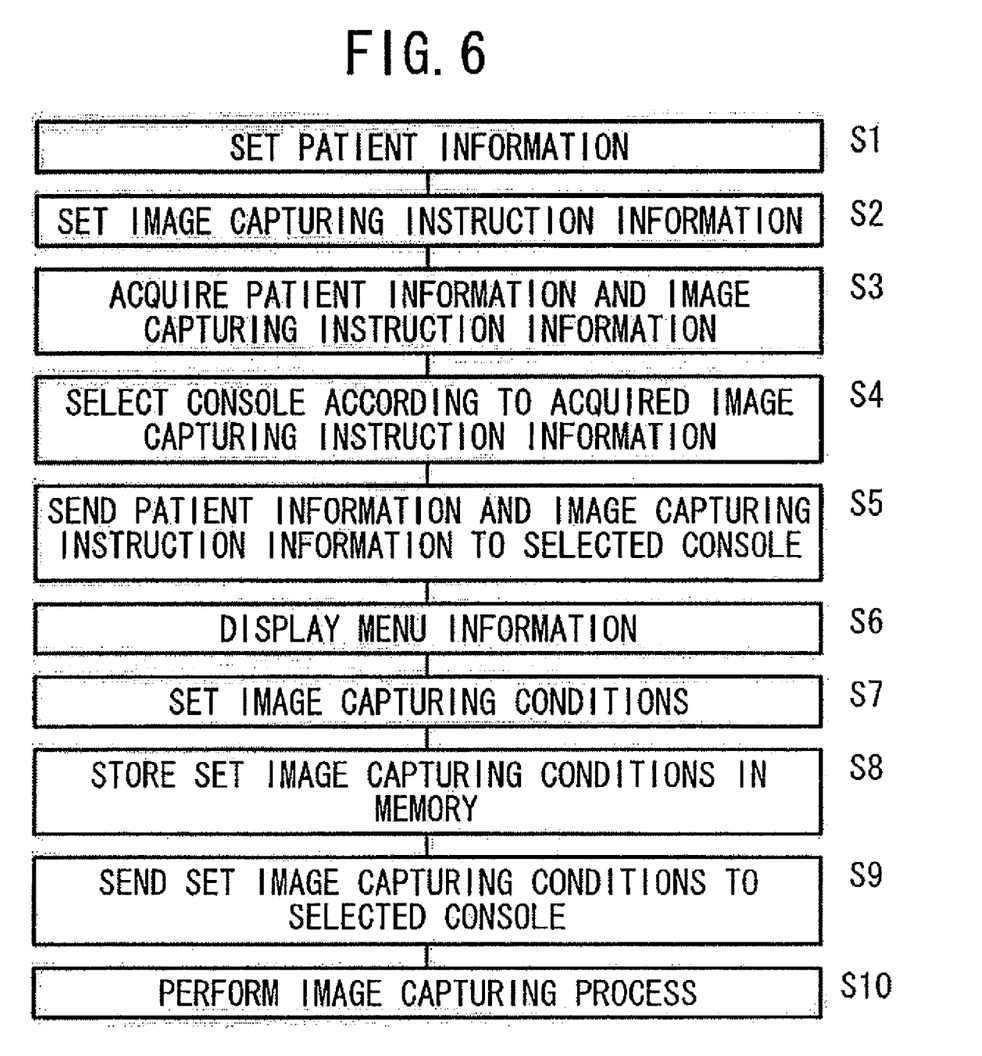
FIG. 6 is a flowchart of a normal operation sequence of the radiation image capturing system.

The controller 34 of the host console 16 that is installed in the radiological department acquires the patient information and the image capturing instruction information from the RIS 14 via the in-house network 28 and stores the patient information and the image capturing instruction information in the image capturing instruction information memory 38 (step S3).

The console selector 41 selects a corresponding console, i.e., the first console 18 for controlling the first image capturing apparatus 22, the second console 20 for controlling the second image capturing apparatus 24, or another console connected to the in-house network 28, according to the acquired image capturing instruction information (step S4).

At this time, the console selector 41 determines whether the console for controlling the image capturing apparatus that is indicated by the image capturing instruction information is capable of performing its processing sequence or not. For example, if the console is controlling the image capturing apparatus to perform an image capturing process or is processing radiation image information acquired from the image capturing apparatus, and hence is unable to immediately perform a next cycle of processing sequence, then the console selector 41 judges that the console is incapable of performing its processing sequence. Furthermore, if the console is suffering a failure or the image capturing apparatus controlled by the console is suffering a failure, then the console selector 41 also judges that the console is incapable of performing its processing sequence. When the console is judged as being incapable of performing its processing sequence, the console selector 41 searches for another console which is capable of capturing radiation image information according to the image capturing instruction information and also of performing its processing sequence.

After the console capable of performing its processing sequence is selected, the controller 34 of the host console 16 sends the patient information and the image capturing instruction information to the first console 18, the second console 20, or another console which has been selected (step S5). If the host console 16 serves as a console capable of performing processing sequences for a plurality of image capturing apparatus of different specifications, then the host console 16 may be selected as a console, instead of the first console 18 or the second console 20, for performing a processing sequence for the first image capturing apparatus 22 or the second image capturing apparatus 24. A doctor may directly select an image capturing apparatus and a console that controls the image capturing apparatus by the RIS 14, not by the console selector 41. In this case, the host console sends the patient information and the image capturing instruction information to the console selected by the doctor.

The controller 34 controls the display unit 48 to display thereon the patient information, the image capturing instruction information and information (identification number for identifying the image capturing apparatus, etc) about the selected image capturing apparatus that have been acquired, as menu information (step S6). Thus, the radiological technician can confirm, at a glance, the image capturing instruction information and which image capturing apparatus should be used (i.e., which console should be operated). The menu information may be displayed on the display units connected to the first console 18 and the second console 20.

Thereafter, the radiological technician sets the image capturing conditions using the manual setting unit 36 of the host console 16 according to the menu information displayed on the display unit 48 (step S7). For example, the radiological technician sets the image capturing conditions corresponding to the body region of the subject 50 to be imaged, with respect to the radiation source of the image capturing apparatus controlled by the selected console. The image capturing conditions include a tube voltage, a tube current and an irradiation time. The setting data (image capturing conditions) that have been input through the manual setting unit 36 are stored in the image capturing condition memory 42 through the image capturing condition setting unit 43 (step S8). The image capturing conditions depending on the body region may be set using the RIS 14. In this case, the image capturing conditions from the RIS 14 are also stored in the image capturing condition memory 42 through the image capturing condition setting unit 43. The set image capturing conditions are sent to the currently-selected console through the in-house network 28 (step S9). As a matter of course, the image capturing conditions may be set using the manual setting unit of the first console 18 or the second console 20. For example, if the selected console is the first console 18, and the image capturing conditions have been set through the manual setting unit of the second console 20, the set image capturing conditions are transmitted to the first console 18 through the in-house network 28. At this time, the image capturing conditions may be transmitted to the first console 18 through the host console 16.

Normally, the console to which the image capturing conditions have been transmitted controls the corresponding image capturing apparatus to capture a radiation image according to the transmitted image capturing conditions (step S10).

There are some cases where the image capturing apparatus needs to be changed due to conditions of the patient or unexpected circumstances. In this case, the image capturing conditions have to be changed. Thus, generally, the radiological technician confirms image capturing conditions appropriate for the changed image capturing apparatus (or both the image capturing apparatus and the body region to be imaged) based on the instruction manual etc., and performs the setting again from the beginning. Such a procedure itself is tedious and time-consuming. Further, the procedure keeps the patient waiting, which results in the mental burden on the patient.

In the image capturing system 10 according to the present invention, the following procedure is performed in order to easily change image capturing conditions. A process for changing image capturing conditions will be explained below with reference to FIG. 7.

The following may be considered as a case where the image capturing conditions need to be changed (the set image capturing apparatus needs to be switched to another image capturing apparatus).

Figure 7:
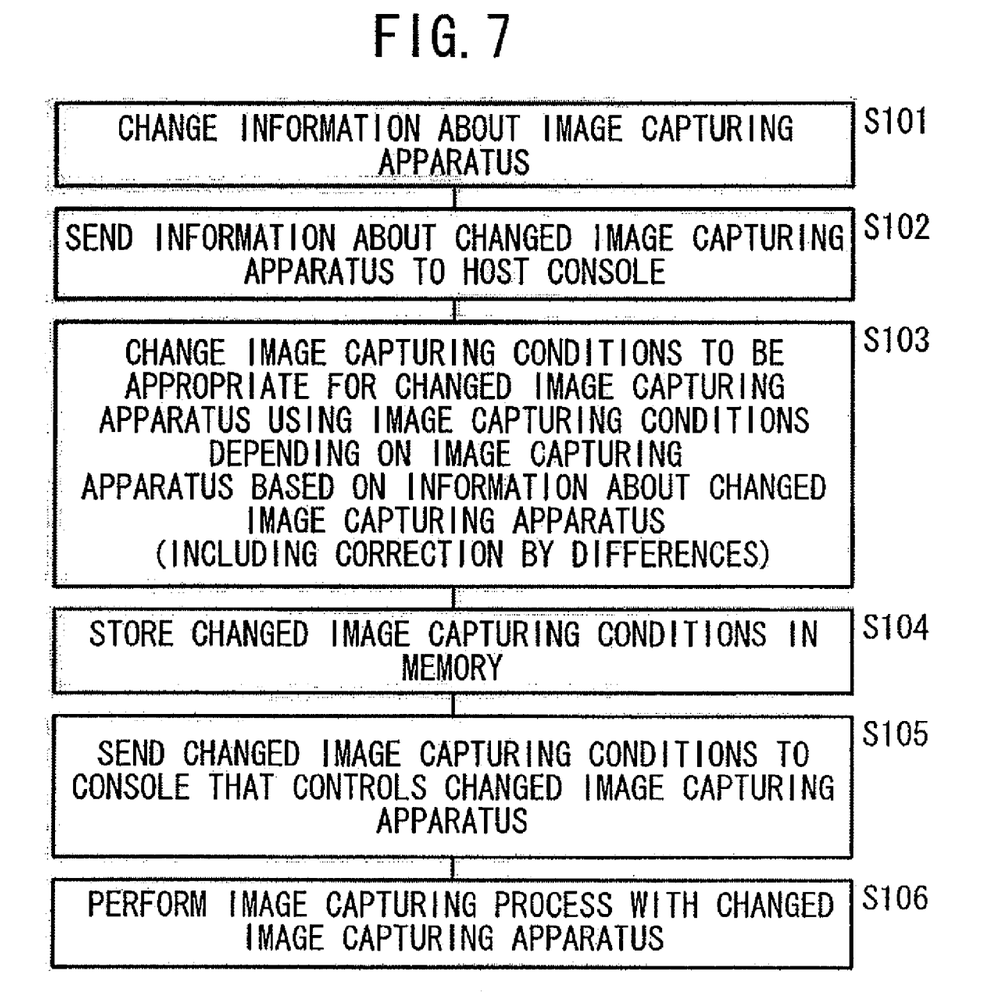
FIG. 7 is a flowchart of an operation sequence for changing image capturing conditions.

The console selector 41 selects the console that controls the first image capturing apparatus 22 or the doctor selects the first image capturing apparatus 22 using the RIS 14, but the subject 50 is using a wheelchair and cannot be imaged by the first image capturing apparatus 22. In this case, the technician places the cassette 110 between the wheelchair and the subject 50, and switches to an image capturing process using the radiation source 104 of the second image capturing apparatus 24 as an alternative. In one case, the console selector 41 selects the console that controls the second image capturing apparatus 24 or the doctor selects the second image capturing apparatus 24, but the second image capturing apparatus 24 cannot be used because of an unexpected occurrence or its adjustment process. In this case, the technician also switches to an image capturing process using the first image capturing apparatus 22 as an alternative.

In such cases, in order to switch the image capturing apparatus, the technician changes information (identification number of the image capturing apparatus etc.) about the image capturing apparatus using the manual setting unit 36 of the host console 16 (step S101 in FIG. 7). The information may be changed using the manual setting unit of the first console 18 or the second console 20. If the information is changed using the manual setting unit of the first console 18 or the second console 20, the changed information is sent to the host console 16 through the in-house network 28 (step S102).

As described above, when information about the image capturing apparatus is changed by the technician, the image capturing condition changer 44 automatically changes the image capturing conditions (i.e., image capturing conditions before changing) set by the image capturing condition setting unit 43, into image capturing conditions appropriate for the changed image capturing apparatus (alternative image capturing apparatus) using the image capturing conditions depending on the image capturing apparatus which are stored in the data memory 45, on the basis of information about the alternative image capturing apparatus (step S103). The changed image capturing conditions are stored in the image capturing condition memory 42 (step S104). If the image capturing conditions are set depending on the image capturing apparatus and the body region to be imaged, the image capturing condition changer 44 automatically changes the image capturing conditions (i.e., image capturing conditions before changing) set by the image capturing condition setting unit 43, into image capturing conditions appropriate for the alternative image capturing apparatus, using the image capturing conditions depending on the image capturing apparatus which are stored in the data memory 45, on the basis of information about the alternative image capturing apparatus and information about the body region of the image capturing instruction information.

Alternatively, differences between image capturing conditions of image capturing apparatus of different specifications may be stored in the data memory 45, a corresponding difference of image capturing conditions is read from the data memory 45 on the basis of the information about the image capturing apparatus before changing and the information about the image capturing apparatus after changing. The set image capturing conditions (image capturing conditions before changing) may be corrected into image capturing conditions for the changed image capturing apparatus, based on the read difference. The difference includes difference values with respect to tube currents, tube voltages, irradiation times, doses, etc. For example, in cases where the first image capturing apparatus 22 has been initially selected, but it is switched to the second image capturing apparatus 24, a difference value with respect to, for example, the irradiation time is read from the data memory 45, and the irradiation time of the initially set image capturing conditions is reduced by subtracting the difference value from the initially-set irradiation time. Further alternatively, the image capturing conditions may be corrected based on the ratio of the sensitivity of the radiation detector to be used.

Since the image capturing conditions are automatically changed only by inputting information (identification number, etc.) about the image capturing apparatus in this manner, even when the doctor recognizes the image capturing conditions for only one of the first image capturing apparatus 22 and the second image capturing apparatus 24, appropriate image capturing conditions for another image capturing apparatus that is not recognized by the technician can be automatically set.

Thereafter, the host console 16 sends the patient information, the image capturing instruction information (including information about the image capturing apparatus after changing), and the changed image capturing conditions to the console that controls the alternate image capturing apparatus (step S105).

The console (i.e., console that controls the alternate image capturing apparatus) to which the patient information, the image capturing instruction information and the changed image capturing conditions have been sent now controls the image capturing apparatus under its control, and performs a process of capturing a radiation image using the image capturing apparatus under its control, according to the changed image capturing conditions (step S106).

First, a process of capturing radiation image information of the subject 50 with the first image capturing apparatus 22 controlled by the first console 18 will be described below with reference to a flowchart of FIG. 8.

Figure 8:
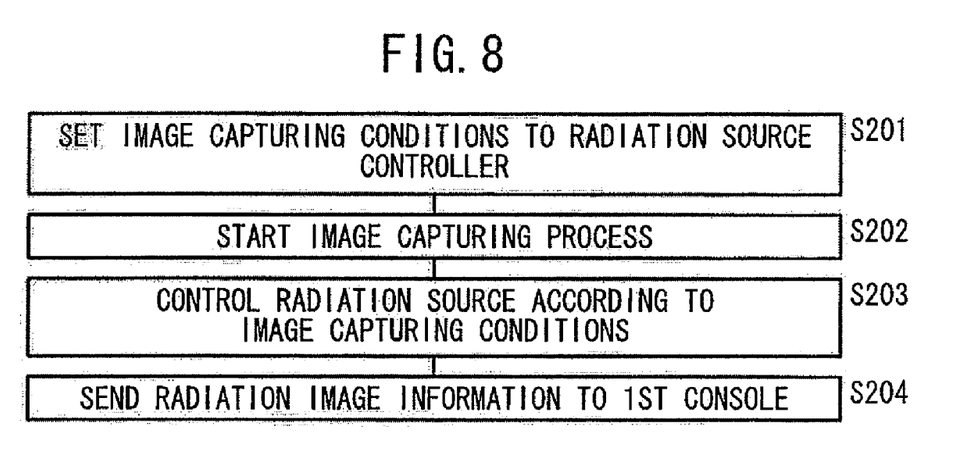
FIG. 8 is a flowchart of an operation sequence of a first console and a first image capturing apparatus.

When the first console 18 receives the image capturing instruction information and the changed image capturing conditions from the host console 16, the first console 18 sets a tube voltage, a tube current, and an irradiation time of the image capturing conditions in the radiation source controller 66 of the first image capturing apparatus 22 (step S201 in FIG. 8).

After having positioned the subject 50 in a given position on the image capturing base 60, the radiological technician operates an image capturing switch, not shown, to start an image capturing process (step S202). The radiation source controller 66 controls the radiation source 64 according to the set image capturing conditions (step S203) to apply the radiation X to the subject 50. The radiation X that has passed through the subject 50 is applied to the radiation detector 70.

The radiation X is converted into electric signals by the photoelectric conversion layer 72 of the pixels 78 of the radiation detector 70 (FIG. 4). The electric signals are stored as electric charges in the storage capacitors 76. The stored electric charges, which represent radiation image information of the subject 50, are read from the storage capacitors 76 according to address signals which are supplied from the controller 100 to the line scanning driver 84 and the multiplexer 86.

Specifically, in response to the address signal supplied from the controller 100, the address decoder 88 of the line scanning driver 84 outputs a selection signal so as to select one of the switches SW1, which supplies the control signal Von to the gates of the TFTs 74 connected to the gate line 80 corresponding to the selected switch SW1. In response to the address signal supplied from the controller 100, the address decoder 96 of the multiplexer 86 outputs a selection signal, which operates to successively turn on the switches SW2 so as to switch between the signal lines 82, for thereby reading the electric charges stored in the storage capacitors 76 of the pixels 78 connected to the selected gate line 80, through the signal lines 82.

The electric charges (radiation image information) read from the storage capacitors 76 of the pixels 78 connected to the selected gate line 80 are amplified by the respective amplifiers 92, sampled by the sample and hold circuits 94, and supplied to the multiplexer 86. Based on the supplied electric charges, the multiplexer 86 generates and supplies a radiation image signal to the A/D converter 98, which converts the radiation image signal into a digital signal. The digital signal which represents the radiation image information is transmitted from the controller 100 to the first console 18 through the in-house network 28 (step S204).

Similarly, the address decoder 88 of the line scanning driver 84 successively turns on the switches SW1 to switch between the gate lines 80 according to the address signal supplied from the controller 100. The electric charges stored in the storage capacitors 76 of the pixels 78 connected to the successively selected gate lines 80 are read through the signal lines 82, and processed by the multiplexer 86 and the A/D converter 98 into digital signals, which are transmitted from the controller 100 to the first console 18 through the in-house network 28 (step S204).

The first console 18 processes the radiation image information represented by the received digital signals depending on the specifications of the first image capturing apparatus 22. Then, the first console 18 displays a radiation image based on the processed radiation image information for the radiological technician to confirm the radiation image, and then transmits the radiation image information to the viewer 15 through the in-house network 28. The doctor then interprets for diagnosis a radiation image that is displayed by the viewer 15 based on the radiation image information. If the first console 18 is processing other radiation image information that has already been received thereby, then the console selector 41 of the host console 16 searches for another processor capable of performing its processing sequence, and sends the radiation image information acquired from the first image capturing apparatus 22 to the retrieved other processor to process the radiation image information.

A process of capturing a chest image of the subject 50 with the second image capturing apparatus 24 controlled by the second console 20 will be described below with reference to a flowchart of FIG. 9.

Figure 9:
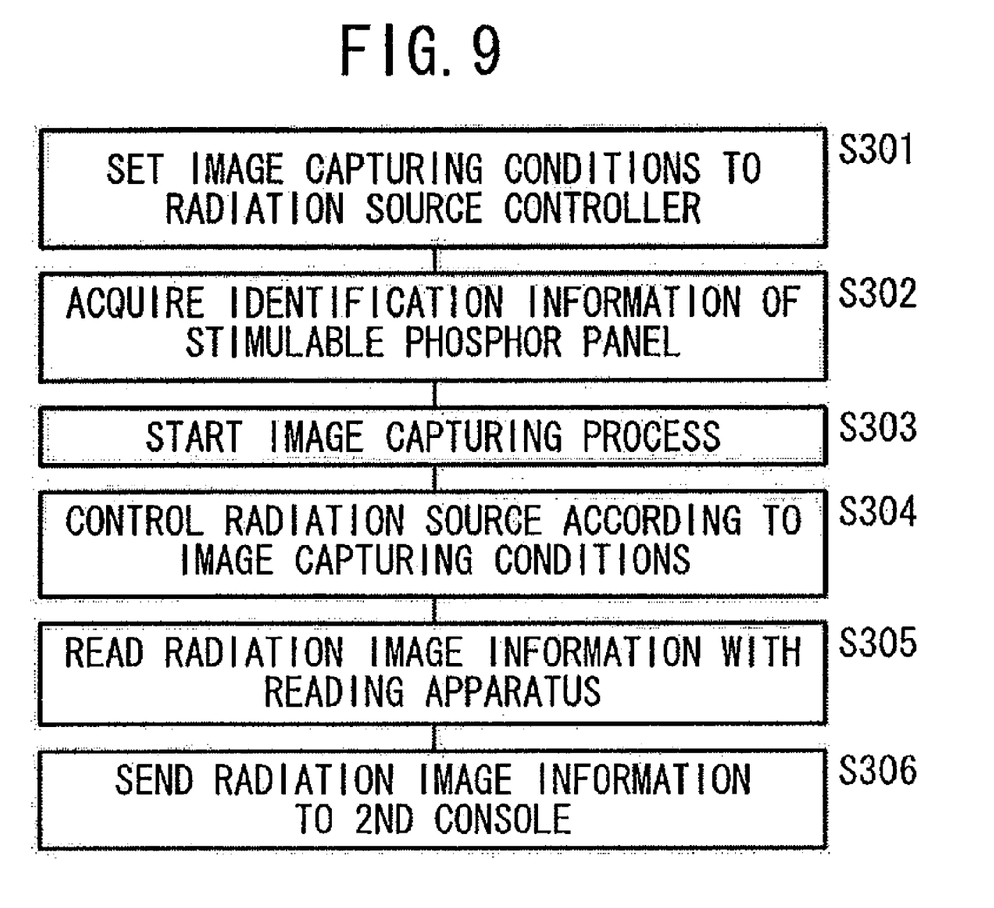
FIG. 9 is a flowchart of an operation sequence of a second console and a second image capturing apparatus.

When the second console 20 receives the image capturing instruction information and the changed image capturing conditions from the host console 16, the second console 20 sets a tube voltage, a tube current, and an irradiation time of the image capturing conditions in the radiation source controller 102 of the second image capturing apparatus 24 (step S301 in FIG. 9).

The radiological technician uses the bar-code reader 32 connected to the second console 20 to read the bar code 116 attached to the cassette 110, thereby acquiring identification information including a unique number for identifying the stimulable phosphor panel P housed in the cassette 110, the size of the stimulable phosphor panel P, the sensitivity of the stimulable phosphor panel P, etc (step S302).

After having loaded the cassette 110 into the slot 112 of the second image capturing apparatus 24, the radiological technician operates an image capturing switch, not shown, to start an image capturing process (step S303). The radiation source controller 102 controls the radiation source 104 according to the set image capturing conditions (step S304) to apply the radiation X to the subject 50. The radiation X that has passed through the subject 50 is applied to the stimulable phosphor panel P housed in the cassette 110. As a result, radiation image information of the subject 50 is recorded in the stimulable phosphor panel P.

The radiological technician then removes the cassette 110 housing therein the stimulable phosphor panel P with the recorded radiation image information, from the second image capturing apparatus 24, and thereafter loads the cassette 110 into the cassette loader 120 of the reading apparatus 26.

When the cassette 110 is loaded into the cassette loader 120, the bar-code reader 124 in the cassette loader 120 reads the bar code 116 attached to the cassette 110 to acquire the identification information including the unique number, the size, the sensitivity, etc. of the stimulable phosphor panel P. The acquired identification information is compared with the identification information read by the bar-code reader 32 connected to the second console 20 to confirm the correspondence between the subject 50 and the radiation image information.

After the identification information is read, the unlock mechanism 126 is actuated to unlock and open the lid member 114. The suction cup 128 attracts the stimulable phosphor panel P, removes the stimulable phosphor panel P out of the cassette 110, and feeds the stimulable phosphor panel P between the nip rollers 130. The stimulable phosphor panel P which is gripped by the nip rollers 130 is then fed to a position beneath the scanning unit 144 through the curved feed path 136 made up of the feed rollers 132a through 132g and the guide plates 134a through 134f.

Beneath the scanning unit 144, the stimulable phosphor panel P is fed substantially horizontally in an auxiliary scanning direction by the feed rollers 132d, 132e. At the same time, the laser beam LB output from the laser oscillator 150 of the stimulator 146 is reflected and deflected by the polygon mirror 152 that is rotating at a high speed, and then guided by the reflecting mirror 154 to the stimulable phosphor panel P whose lower surface is supported by the platen roller 142, thereby scanning the stimulable phosphor panel P in a main scanning direction.

By being irradiated with the laser beam LB, the stimulable phosphor panel P is stimulated to emit stimulated light representative of the radiation image information recorded therein. The stimulated light is applied directly or via the light collecting mirror 160 to the lower end of the light guide 156 which is disposed near the stimulable phosphor panel P and extends in the main scanning direction. The stimulated light which has entered the light guide 156 is repeatedly reflected in the light guide 156 and guided to the photomultiplier 158. The photomultiplier 158 converts the stimulated light into an electric signal representative of the radiation image information recorded in the stimulable phosphor panel P. In this manner, the radiation image information recorded in the stimulable phosphor panel P is read by the scanning unit 144 of the reading apparatus 26 (step S305).

The radiation image information thus read by the scanning unit 144 is transmitted to the second console 20 through the in-house network 28 (step S306). The second console 20 processes the received radiation image information depending on the specifications of the second image capturing apparatus 24. Then, the second console 20 displays a radiation image based on the processed radiation image information for the radiological technician to confirm the radiation image, and then transmits the radiation image information to the viewer 15 through the in-house network 28. The doctor then interprets for diagnosis a radiation image that is displayed by the viewer 15 based on the radiation image information. If the second console 20 is processing other radiation image information that has already been received thereby, then the console selector 41 of the host console 16 searches for another processor capable of performing its processing sequence, and sends the radiation image information acquired from the second image capturing apparatus 24, to the retrieved other processor to process the radiation image information.

As described above, in the present embodiment, in cases where image capturing conditions have been set to be appropriate for an image capturing apparatus selected on the basis of image capturing instruction information and the like, and thereafter the image capturing apparatus is changed depending on situations, the set image capturing conditions can be automatically changed to image capturing conditions appropriate for the changed image capturing apparatus (alternative apparatus) only by inputting, for example, the identification number of the image capturing apparatus. Thus, image capturing conditions can easily be changed, and also, desired radiation image information can be obtained by the changed image capturing apparatus. For example, when the image capturing apparatus to be used is switched to an image capturing apparatus which incorporates a radiation detector of high sensitivity, the radiation image capturing system is capable of automatically reducing the dose of a radiation to be applied to the subject without requiring the radiological technician in charge of the radiation image capturing system to perform a tedious and time-consuming procedure for changing the dose of the radiation. As a result, operating efficiency for a radiation image capturing process is improved, inconvenience such as keeping the patient waiting for a long time is prevented, and a work burden of the radiological technician is reduced.

Although a certain preferred embodiment of the present invention has been shown and described in detail, it should be understood that various changes and modifications may be made therein without departing from the scope of the appended claims.

Specifically, the radiation detector 70 is a direct-conversion type of radiation detector which directly converts the applied radiation X into an electric signal with the photoelectric conversion layer 72. Instead of the direct-conversion type, the present invention may employ an indirect-conversion type of radiation detector including a scintillator for converting the applied radiation X into visible light and a solid-state detecting device such as of amorphous silicon (a-Si) or the like for converting the visible light into an electric signal (see Japanese Patent No. 3494683).

Further, the present invention may employ a light readout type of radiation detector for acquiring radiation image information. The light readout type of radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices, which generate an electric current, and the electric current is acquired as radiation image information. After the radiation image information has been read, if erasing light is applied to the radiation detector, radiation image information representing a residual electrostatic latent image is erased from the radiation detector, which can thus be reused (see Japanese Laid-Open Patent Publication No. 2000-105297).

In the above embodiment, the radiation detector 70 employs TFTs 74. Alternatively, the TFT 74 may be combined with other imaging devices such as a CMOS (Complementary Metal-Oxide Semiconductor) image sensor. Further, a CCD (Charge-Coupled Device) image sensor which transfers electric charges while shifting them with shift pulses corresponding to the gate signals for the TFTs 74 may be used. Still further, in the above embodiment, patient information is acquired through the HIS 12, and image capturing instruction information is acquired through the RIS 14. Alternatively, the patient information and the image capturing instruction information may be input using a keyboard or a coordinate input device connected to the host console or other consoles.

What is claimed is:

1. A radiation image capturing system comprising:
    a plurality of image capturing apparatus of different specifications for capturing a radiation image of a subject;
    a plurality of processors disposed corresponding to each of the image capturing apparatus, the processors controlling the corresponding image capturing apparatus, respectively;
    a processor selector for selecting one processor from among the processors based on supplied image capturing instruction information;
    an image capturing condition setting unit for setting the image capturing conditions to be appropriate for an image capturing apparatus that is controlled by the processor selected by the processor selector among the plurality of image capturing apparatus; and
    an image capturing condition changer for, in a case where the image capturing apparatus is changed, changing the image capturing conditions to be appropriate for the changed image capturing apparatus,
    wherein the processor corresponding to the changed image capturing apparatus controls the changed image capturing apparatus according to the changed image capturing conditions.

2. A radiation image capturing system according to claim 1, further comprising a data memory for storing the image capturing conditions depending on each of the image capturing apparatus,
    wherein the image capturing condition changer reads the image capturing conditions depending on the changed image capturing apparatus from the data memory, and sets the read image capturing conditions as the image capturing conditions for the changed image capturing apparatus.

3. A radiation image capturing system according to claim 1, further comprising a data memory for storing differences of the image capturing conditions between the image capturing apparatus of different specifications,
    wherein the image capturing condition changer reads the differences of the image capturing conditions from the data memory on the basis of information about the image capturing apparatus before changing and information about the changed image capturing apparatus, corrects the image capturing conditions before changing into image capturing conditions for the changed image capturing apparatus on the basis of the read differences, and sets the corrected image capturing conditions as the image capturing conditions for the changed image capturing apparatus.

4. A radiation image capturing system according to claim 1, further comprising a data memory for storing the image capturing conditions depending on each of the image capturing apparatus,
    wherein the image capturing condition setting unit sets the image capturing conditions depending on an image capturing apparatus that is controlled by a processor selected by the processor selector, and a body region to be imaged, and
    the image capturing condition changer changes the image capturing conditions set by the image capturing condition setting unit into image capturing conditions appropriate for the changed image capturing apparatus using the image capturing conditions corresponding to the changed image capturing apparatus which are stored in the data memory, on the basis of information about the changed image capturing apparatus and information about the body region of the image capturing instruction information.

5. A radiation image capturing system according to claim 1, further comprising a managing apparatus incorporating the image capturing condition changer, for managing the processors,
    wherein the image capturing condition changer changes the image capturing conditions to be appropriate for the changed image capturing apparatus on the basis of information about the changed image capturing apparatus set in any one of the processors and the managing apparatus, and
    the managing apparatus sends the changed image capturing conditions to a processor that controls the changed image capturing apparatus.

6. A radiation image capturing method of capturing a radiation image with a radiation image capturing system comprising a plurality of image capturing apparatus of different specifications for capturing a radiation image of a subject and a plurality of processors disposed corresponding to each of the image capturing apparatus, the processors controlling the corresponding image capturing apparatus, respectively, the method comprising the steps of:
    selecting one processor from among the processors based on supplied image capturing instruction information;
    setting the image capturing conditions to be appropriate for an image capturing apparatus that is controlled by the processor selected in the step of selecting one processor from among the plurality of image capturing apparatus;
    in the case where the image capturing apparatus is changed, changing the image capturing conditions to be appropriate for the changed image capturing apparatus; and
    controlling the changed image capturing apparatus according to the changed image capturing conditions.

7. A radiation image capturing method according to claim 6, wherein the radiation image capturing system comprises a data memory for storing the image capturing conditions depending on each of the image capturing apparatus, and
    in the step of changing the image capturing conditions, the image capturing conditions depending on the changed image capturing apparatus are read from the data memory, and the read image capturing conditions are set as the image capturing conditions for the changed image capturing apparatus.

8. A radiation image capturing method according to claim 6, wherein the radiation image capturing system comprises a data memory for storing differences of the image capturing conditions between the image capturing apparatus of different specifications, and in the step of changing the image capturing conditions, the differences of the image capturing conditions are read from the data memory on the basis of information about the image capturing apparatus before changing and information about the changed image capturing apparatus, the image capturing conditions before changing are corrected into image capturing conditions for the changed image capturing apparatus on the basis of the read differences, and the corrected image capturing conditions are set as the image capturing conditions for the changed image capturing apparatus.

9. A radiation image capturing method according to claim 6, wherein the radiation image capturing system further comprises a data memory for storing the image capturing conditions depending on each of the image capturing apparatus, in the step of setting the image capturing conditions, the image capturing conditions are set depending on an image capturing apparatus that is controlled by the processor selected in the step of selecting one processor, and a body region to be imaged, and in the step of changing the image capturing conditions, the image capturing conditions set in the step of setting the image capturing conditions are changed into image capturing conditions appropriate for the changed image capturing apparatus using the image capturing conditions corresponding to the changed image capturing apparatus which are stored in the data memory, on the basis of information about the changed image capturing apparatus and information about the body region of the image capturing instruction information.

10. A radiation image capturing method according to claim 6, wherein the radiation image capturing system comprises a managing apparatus for managing the processors, and in the step of changing the image capturing conditions, the image capturing conditions are changed to be appropriate for the changed image capturing apparatus on the basis of information about the changed image capturing apparatus set in any one of the processors and the managing apparatus, the method further comprising the step of sending the changed image capturing conditions to a processor that controls the changed image capturing apparatus.

* * * * *